United States Patent [19]

Johnson et al.

[11] 4,174,441
[45] Nov. 13, 1979

[54] PYRAN ANALOGS OF 5-HYDROXY-PGI$_1$

[75] Inventors: Roy A. Johnson; John C. Sih, both of Kalamazoo, Mich.

[73] Assignee: The Upjohn Company, Kalamazoo, Mich.

[21] Appl. No.: 899,197

[22] Filed: Apr. 24, 1978

Related U.S. Application Data

[63] Continuation-in-part of Ser. No. 815,648, Jul. 14, 1977, Pat. No. 4,110,532.

[51] Int. Cl.$^2$ .......................................... C07D 311/94
[52] U.S. Cl. .................................... 542/426; 542/421; 542/416; 542/429; 260/343.21; 260/343.5; 260/345.2

[58] Field of Search ............. 260/345.2, 343.21, 343.5; 542/421, 426, 429

[56] References Cited

PUBLICATIONS

Johnson et al., J.A.C.S. 99:12, Jun. 8, 1977, pp. 4182–4184.

Primary Examiner—Natalie Trousof
Assistant Examiner—Bernard Dentz
Attorney, Agent, or Firm—Robert A. Armitage

[57] ABSTRACT

The present invention provides pyran analogs of 5-hydroxy-PGI$_1$, which are useful pharmacological agents. These analogs of prostaglandin I$_1$ are useful for the stimulation of mammalian smooth muscle tissues.

94 Claims, No Drawings

PYRAN ANALOGS OF 5-HYDROXY-PGI$_1$

CROSS REFERENCE TO RELATED APPLICATIONS

This application is a continuation-in-part of Ser. No. 815,648, filed July 14, 1977, issued as U.S. Pat. No. 4,110,532 on Aug. 29, 1978.

The present invention relates to pyran analogs of 5-hydroxy PGI$_1$, the essential material constituting a disclosure thereof being hereby incorporated by reference from U.S. Pat. No. 4,110,532, issued Aug. 29, 1978. In particular the present invention relates to pyran analogs of 5-hydroxy-PGI$_1$ corresponding to the various carboxylic acids disclosed and claimed in U.S. Pat. No. 4,110,532.

We claim:

1. A prostacyclin analog of the formula

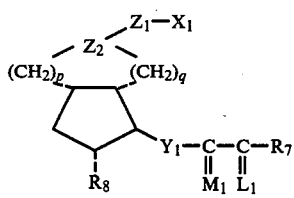

wherein Z$_2$ is

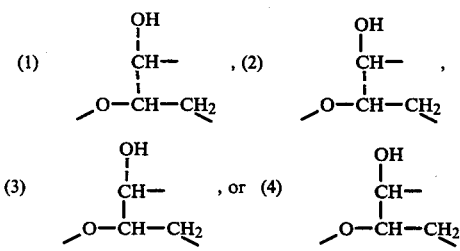

wherein one of p or q is the integer one and the other is the integer zero;
wherein Z$_1$ is
  (1) —(CH$_2$)$_g$—CH$_2$—CH$_2$—,
  (2) —(CH$_2$)$_g$—CH$_2$—CF$_2$—, or
  (3) trans—(CH$_2$)$_g$—CH=CH—,
  wherein g is the integer one, 2, or 3 when q is zero and zero, one, or 2 when q is one;
wherein R$_8$ is hydrogen, hydroxy, or hydroxymethyl;
wherein Y$_1$ is
  (1) trans—CH=CH—,
  (2) cis—CH=CH—,
  (3) —CH$_2$CH$_2$—,
  (4) trans—CH=C(Hal)—, or
  (5) —C≡C—
  wherein Hal is chloro or bromo;
wherein M$_1$ is

or a mixture of

wherein R$_5$ is hydrogen or alkyl with one to 4 carbon atoms, inclusive;
wherein L$_1$ is

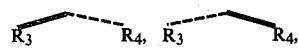

or a mixture of

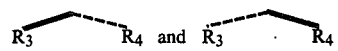

wherein R$_3$ and R$_4$ are hydrogen, methyl, or fluoro, being the same or different, with the proviso that one of R$_3$ and R$_4$ is fluoro only when the other is hydrogen or fluoro;
wherein X$_1$ is
  (1) —COOR$_1$; wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
  (2) —CH$_2$OH,
  (3) —CH$_2$NL$_2$L$_3$, wherein L$_2$ and L$_3$ are hydrogen, alkyl of one to 4 carbon atoms, inclusive, or —COOR$_1$, wherein R$_1$ is as defined above;
  (4) —COL$_4$, wherein L$_4$ is
    (a) amino of the formula —NR$_{21}$R$_{22}$, wherein R$_{21}$ and R$_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl or one to 3 carbon atoms, inclusive, or phenyl substituted with hydroxycarbonyl or alkoxycarbonyl of one to 4 carbon atoms, inclusive;
    (b) carbonylamino of the formula —NR$_{23}$COR$_{21}$, wherein R$_{23}$ is hydrogen or alkyl or one to 4 carbon atoms and R$_{21}$ is as defined above; or
    (c) sulfonylamino of the formula —NR$_{23}$SO$_2$R$_{21}$, wherein R$_{21}$ and R$_{23}$ are as defined above; or
  (5) —COOL$_5$, wherein L$_5$ is p-substituted phenyl selected from the group consisting of

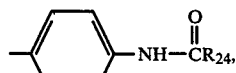

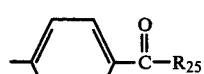

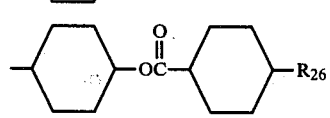

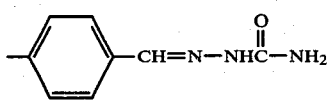

wherein $R_{24}$ is methyl, phenyl, acetamidophenyl, benzamidophenyl, or —NH$_2$; $R_{25}$ is methyl, phenyl, —NH$_2$, of methoxy; and $R_{26}$ is hydrogen or acetamido; and
wherein $R_7$ is
(1) —(CH$_2$)$_3$—CH$_3$,

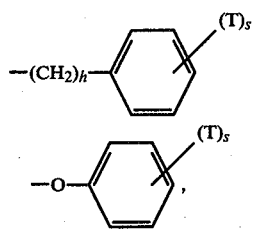

wherein h is the integer zero or one; s is the integer zero, one, 2, or 3; and T is chloro, fluoro, trifluoromethyl, alkyl of one to 3 carbon atoms, inclusive, or with the proviso that not more than two T's are other than alkyl and the 1,5- and 1,15-lactones thereof.

2. A prostacyclin analog according to claim 1 wherein p is one.

3. A prostacyclin analog according to claim 2, wherein $R_8$ is hydroxymethyl.

4. (5S,6S)-11-Deoxy-11α-hydroxymethyl-5-hydroxy-9-deoxy-6,9α-epoxymethylene-PGF$_1$, a prostacyclin analog according to claim 3.

5. A prostacyclin analog according to claim 2, wherein $R_8$ is hydrogen.

6. (5S,6S)-11-Deoxy-5-hydroxy-9-deoxy-6,9α-epoxymethylene-PGF$_1$, a prostacyclin analog according to claim 5.

7. A prostacyclin analog according to claim 2, wherein $R_8$ is hydroxy.

8. A prostacyclin analog according to claim 7, wherein $Z_2$ is

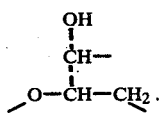

9. A prostacyclin analog according to claim 7, wherein $Z_2$ is

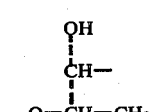

10. (5R,6R)-5-Hydroxy-9-deoxy-6,9α-epoxymethylene-PGF$_1$, a prostacyclin analog according to claim 9.

11. A prostacyclin analog according to claim 7, wherein $Z_2$ is

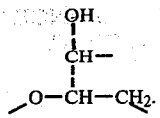

12. (5S,6S)-5-Hydroxy-9-deoxy-6,9α-epoxymethylene-PGF$_1$, a prostacyclin analog according to claim 11.

13. (5S,6S)-5-Hydroxy-9-deoxy-6,9α-epoxymethylene-PGF$_1$, methyl ester, a prostacyclin analog according to claim 11.

14. (5S,6S)-5-Hydroxy-15-methyl-9-deoxy-6,9α-epoxymethylene-PGF$_1$, a prostacyclin analog according to claim 11.

15. (5S,6S)-5-Hydroxy-16,16-dimethyl-9-deoxy-6,9α-epoxymethylene-PGF$_1$, a prostacyclin analog according to claim 11.

16. A prostacyclin analog according to claim 7, wherein $Z_2$ is

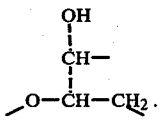

17. A prostacyclin analog according to claim 16, wherein $Y_1$ is cis—CH=CH—.

18. (5R,6S)-5-Hydroxy-cis-13-9-deoxy-6,9α-epoxymethylene-PGF$_1$, a prostacyclin analog according to claim 17.

19. A prostacyclin analog according to claim 16, wherein $Y_1$ is —C≡C—.

20. (5R,6S)-5-Hydroxy-13,14-didehydro-9-deoxy-6,9α-epoxymethylene-PGF$_1$, a prostacyclin analog according to claim 19.

21. A prostacyclin analog according to claim 16, wherein $Y_1$ is trans—CH=C(Hal).

22. (5R,6S)-5-Hydroxy-14-chloro-9-deoxy-6,9α-epoxymethylene-PGF$_1$, a prostacyclin analog according to claim 21.

23. A prostacyclin analog according to claim 16, wherein $Y_1$ is —CH$_2$CH$_2$—.

24. (5R,6S)-5-Hydroxy-13,14-dihydro-9-deoxy-6,9α-epoxymethylene-PGF$_1$, a prostacyclin analog according to claim 23.

25. A prostacyclin analog according to claim 16, wherein $Y_1$ is trans—CH=CH—.

26. A prostacyclin analog according to claim 25, wherein $Z_1$ is —(CH$_2$)$_g$—CH$_2$—CF$_2$.

27. 2,2-Difluoro-(5R,6S)-5-hydroxy-9-deoxy-6,9α-epoxymethylene-PGF$_1$, a prostacyclin analog according to claim 26.

28. A prostacyclin analog according to claim 25, wherein $Z_1$ is trans-(CH$_2$)$_g$—CH=CH—.

29. Trans-2,3-didehydro-(5R,6S)-5-hydroxy-9-deoxy-6,9α-epoxymethylene-PGF$_1$, a prostacyclin analog according to claim 28.

30. A prostacyclin analog according to claim 25, wherein $Z_1$ is —(CH$_2$)$_g$—CH$_2$—CH$_2$—.

31. A prostacyclin analog according to claim 30, wherein g is zero.

32. A prostacyclin analog according to claim 31, wherein $R_7$ is

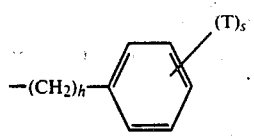

33. (5R,6S)-5-Hydroxy-17-phenyl-18,19,20-trinor-9-deoxy-6,9α-epoxymethylene-PGF₁, a prostacyclin analog according to claim 32.

34. A prostacyclin analog according to claim 31, wherein R₇ is

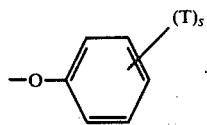

35. (5R,6S)-5-Hydroxy-16-phenoxy-17,18,19,20-tetranor-9-deoxy-6,9α-epoxymethylene-PGF₁, a prostacyclin analog according to claim 34.

36. A prostacyclin analog according to claim 31, wherein R₇ is —(CH₂)$_m$—CH₃.

37. A prostacyclin analog according to claim 36, wherein m is 3.

38. A prostacyclin analog according to claim 37, wherein X₆ is —COL₄.

39. (5R,6S)-5-Hydroxy-9-deoxy-6,9α-epoxymethylene-PGF₁, amide, a prostacyclin analog according to claim 38.

40. A prostacyclin analog according to claim 38, wherein X₆ is —CH₂OH.

41. 2-Decarboxy-2-hydroxymethyl-(5R,6S)-5-hydroxy-9-deoxy-6,9α-epoxymethylene-PGF₁, a prostacyclin analog according to claim 40.

42. A prostacyclin analog according to claim 37, wherein X₆ is —COOR₁.

43. A prostacyclin analog according to claim 42, wherein R₅ is methyl.

44. (5R,6S)-5-Hydroxy-15-methyl-9-deoxy-6,9α-epoxymethylene-PGF₁, a prostacyclin analog according to claim 43.

45. A prostacyclin analog according to claim 42, wherein R₅ is hydrogen.

46. A prostacyclin analog according to claim 45, wherein at least one of R₃ and R₄ is fluoro.

47. (5R,6S)-5-Hydroxy-16,16-difluoro-9-deoxy-6,9α-epoxymethylene-PGF₁, a prostacyclin analog according to claim 46.

48. A prostacyclin analog according to claim 45, wherein at least one of R₃ and R₄ is methyl.

49. (5R,6S)-5-Hydroxy-16,16-dimethyl-9-deoxy-6,9α-epoxymethylene-PGF₁, a prostacyclin analog according to claim 48.

50. A prostacyclin analog according to claim 45, wherein R₃ and R₄ are both hydrogen.

51. (5R,6S)-5-Hydroxy-9-deoxy-6,9α-epoxymethylene-PGF₁, methyl ester, a prostacyclin analog according to claim 50.

52. (5R,6S)-5-Hydroxy-9-deoxy-6,9α-epoxymethylene-PGF₁, tris(hydroxymethyl)aminomethane salt, a prostacyclin analog according to claim 50.

53. (5R,6S)-5-Hydroxy-9-deoxy-6,9α-epoxymethylene-PGF₁, adamantanamine salt, a prostacyclin analog according to claim 50.

54. (5R,6S)-5-Hydroxy-9-deoxy-6,9α-epoxymethylene-PGF₁, a prostacyclin analog according to claim 50.

55. A prostacyclin analog according to claim 1, wherein q is one.

56. A prostacyclin analog according to claim 55, wherein Z₂ is

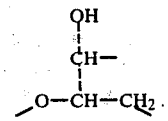

57. A prostacyclin analog according to claim 56, wherein Y₁ is cis—CH=CH—.

58. (4R,5S)-4-Hydroxy-cis-13-5,9α-epoxy-PGF₁, a prostacyclin analog according to claim 57.

59. A prostacyclin analog according to claim 56, wherein Y₁ is —C≡C—.

60. (4R,5S)-4-Hydroxy-13,14-didehydro-5,9α-epoxy-PGF₁, a prostacyclin analog according to claim 59.

61. A prostacyclin analog according to claim 56, wherein Y₁ is trans—CH=C(Hal)—.

62. (4R,5S)-4-Hydroxy-14-chloro-5,9α-epoxy-PGF₁, a prostacyclin analog according to claim 61.

63. A prostacyclin analog according to claim 56, wherein Y₁ is —CH₂CH₂—.

64. (4R,5S)-4-Hydroxy-13,14-dihydro-5,9α-epoxy-PGF₁, a prostacyclin analog according to claim 63.

65. A prostacyclin analog according to claim 56, wherein Y₁ is trans—CH=CH—.

66. A prostacyclin analog according to claim 65, wherein Z₁ is —(CH₂)$_g$—CH₂—CF₂.

67. 2,2-Difluoro-(4R,5S)-4-hydroxy-5,9α-epoxy-PGF₁, a prostacyclin analog according to claim 66.

68. A prostacyclin analog according to claim 65, wherein Z₁ is trans-(CH₂)$_g$—CH=CH—.

69. Trans-2,3-didehydro-(4R,5S)-4-hydroxy-5,9α-epoxy-PGF₁, a prostacyclin analog according to claim 68.

70. A prostacyclin analog according to claim 65, wherein Z₁ is —(CH₂)$_g$—CH₂—CH₂—.

71. A prostacyclin analog according to claim 70, wherein g is zero.

72. A prostacyclin analog according to claim 71, wherein R₇ is

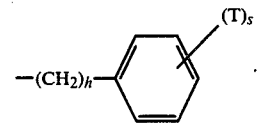

73. (4R,5S)-4-Hydroxy-17-phenyl-18,19,20-trinor-5,9α-epoxy-PGF₁, a prostacyclin analog according to claim 72.

74. A prostacyclin analog according to claim 71, wherein R₇ is

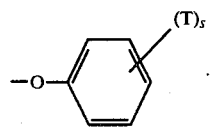

75. (4R,5S)-4-Hydroxy-16-phenoxy-17,18,19,20-tetranor-5,9α-epoxy-PGF₁, a prostacyclin analog according to claim 74.

76. A prostacyclin analog according to claim 71, wherein $R_7$ is —$(CH_2)_m$—$CH_3$.

77. A prostacyclin analog according to claim 76, wherein m is 3.

78. A prostacyclin analog according to claim 77, wherein $X_6$ is —$COL_4$.

79. (4R,5S)-4-Hydroxy-5,9α-epoxy-PFG$_1$, amide a prostacyclin analog according to claim 78.

80. A prostacyclin analog according to claim 78, wherein $X_6$ is —$CH_2OH$.

81. 2-Decarboxy-2-hydroxymethyl-(4R,5S)-4-hydroxy-5,9α-epoxy-PGF$_1$, a prostacyclin analog according to claim 80.

82. A prostacyclin analog according to claim 77, wherein $X_1$ is —$COOR_1$.

83. A prostacyclin analog according to claim 82, wherein $R_5$ is methyl.

84. (4R,5S)-4-Hydroxy-15-methyl-5,9α-epoxy-PGF$_1$, a prostacyclin analog according to claim 43.

85. A prostacyclin analog according to claim 82, wherein $R_5$ is hydrogen.

86. A prostacyclin analog according to claim 85, wherein at least one of $R_3$ and $R_4$ is fluoro.

87. (4R,5S)-4-Hydroxy-16,16-difluoro-5,9α-epoxy-PGF$_1$, a prostacyclin analog according to claim 86.

88. A prostacyclin analog according to claim 85, wherein at least one of $R_3$ and $R_4$ is methyl.

89. (4R,5S)-4-Hydroxy-16,16-dimethyl-5,9α-dimethyl-(5,9α-epoxy-PGF$_1$, a prostacyclin analog according to claim 88.

90. A prostacyclin analog according to claim 85, wherein $R_3$ and $R_4$ are both hydrogen.

91. (4R,5S)-4-Hydroxy-5,9α-epoxy-PGF$_1$, methyl ester, a prostacyclin analog according to claim 90.

92. (4R,5S)-4-Hydroxy-5,9α-epoxy-PGF$_1$, tris(hydroxymethyl)aminomethane salt, a prostacyclin analog according to claim 90.

93. (4R,5S)-4-Hydroxy-5,9α-epoxy-PGF$_1$, adamantanamine salt, a prostacyclin analog according to claim 90.

94. (4R,5S)-4-Hydroxy-5,9α-epoxy-PGF$_1$, a prostacyclin analog according to claim 90.

* * * * *

UNITED STATES PATENT OFFICE
CERTIFICATE OF CORRECTION

Patent No. 4,174,441　　　　　　　　　　　Dated　　13 November 1979

Inventor(s) Roy A. Johnson and John C. Sih

It is certified that error appears in the above-identified patent and that said Letters Patent are hereby corrected as shown below:

Column 1, lines 18-22 should be deleted.

Column 1, line 63 through Column 2, line 5, should be deleted and should read

Column 3, line 10, "of methoxy" should read -- or methoxy --; lines 48-53,

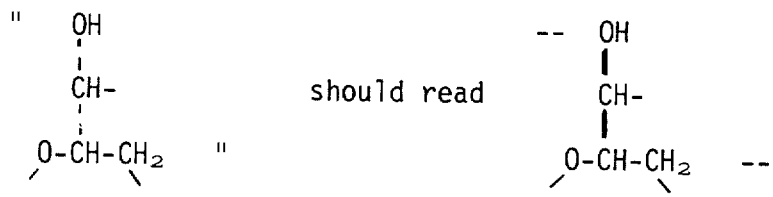

Column 3, lines 58-63,

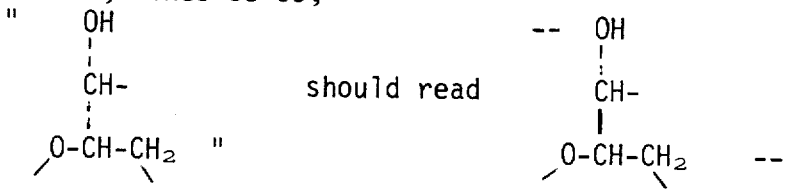

Column 4, lines 1-7,

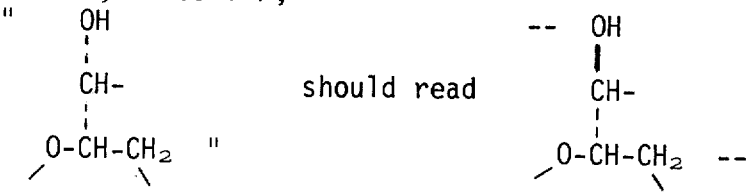

UNITED STATES PATENT OFFICE
CERTIFICATE OF CORRECTION

Patent No. 4,174,441  Dated 13 November 1979

Inventor(s) Roy A. Johnson and John C. Sih

It is certified that error appears in the above-identified patent and that said Letters Patent are hereby corrected as shown below:

Column 5, line 28, line 33, and line 38, "wherein $X_6$ is" should read -- wherein $X_1$ is --;

Column 7, line 6 and line 10, "wherein $X_6$ is" should read -- wherein $X_1$ is --

Column 8, lines 7-8, "5,9α-dimethyl-(5,9α-epoxy" should read -- 5,9α-epoxy --.

Column 4, line 66, "wherein g is zero." should read -- wherein g is one. -- Column 7, line 7, "$PFG_1$" should read -- $PGF_1$ --; line 20, "claim 43" should read -- claim 84 --.

Signed and Sealed this

Thirtieth Day of September 1980

[SEAL]

Attest:

SIDNEY A. DIAMOND

Attesting Officer   Commissioner of Patents and Trademarks